(12) United States Patent
Chu et al.

(10) Patent No.: US 6,277,584 B1
(45) Date of Patent: Aug. 21, 2001

(54) METHOD FOR CALIBRATING A CHEMICAL ANALYZER WITH IMPROVED ACCURACY AT LOW SIGNAL LEVELS

(75) Inventors: Victor Pichai Chu, Hockessin; Connie Mary Sanders, Newark, both of DE (US); James Floyd Pierson-Perry, Elkton, MD (US); Tie Quan Wei, Bear, DE (US)

(73) Assignee: Dade Behring Inc., Deerfield, IL (US)

( * ) Notice: Subject to any disclaimer, the term of this patent is extended or adjusted under 35 U.S.C. 154(b) by 0 days.

(21) Appl. No.: 09/212,641

(22) Filed: Dec. 16, 1998

(51) Int. Cl.[7] .................................................. G01N 33/53
(52) U.S. Cl. .......................... 435/7.1; 435/7.9; 435/7.92; 435/967; 436/513; 436/811; 436/815
(58) Field of Search ........................ 435/7.1, 7.9, 7.92, 435/967; 436/513, 811, 815

(56) References Cited

U.S. PATENT DOCUMENTS

| | | | |
|---|---|---|---|
| 3,960,497 | 6/1976 | Acord | 23/253 R |
| 4,043,756 | 8/1977 | Sommervold | 23/230 R |
| 4,169,125 | 9/1979 | Rodriguez et al. | 422/65 |
| 4,706,207 | 11/1987 | Hennessy et al. | 364/555 |
| 5,083,283 | 1/1992 | Imai et al. | 364/497 |
| 5,281,540 | 1/1994 | Merkh et al. | 436/530 |
| 5,348,889 | 9/1994 | Terashima et al. | 436/8 |
| 5,554,539 | 9/1996 | Chadney et al. | 436/8 |
| 5,795,791 | 8/1998 | Hirai et al. | 436/501 |

*Primary Examiner*—Christopher L. Chin
(74) *Attorney, Agent, or Firm*—Leland K. Jordan

(57) ABSTRACT

Calibration of an assay by converting an analyzer's normal signal response through an arithmetic function prior to performing the curve fit, thereby improving the accuracy of the curve fit in a region of greatest diagnostic interest.

14 Claims, 6 Drawing Sheets

METHOD FOR CALIBRATING A CHEMICAL ANALYZER WITH IMPROVED ACCURACY AT LOW SIGNAL LEVELS

BACKGROUND OF THE INVENTION

1. Field of the Invention

The present invention relates an improved calibration method to provide increased accuracy for in vitro chemical diagnostic tests where analyte concentrations of clinical relevance result in low assay signal values. In particular, the invention provides for improved accuracy in the region of a calibration curve corresponding to low measured signal values without utilization of a mathematical weighting routine.

2. Description of the Related Art

Generally, biochemical analyzers employ a combination of analyte specific chemical reagents and reaction monitoring means to assay or determine the presence or concentration of a specific substance or analyte within a liquid sample suspected of containing that particular analyte. Such analyzers are well known and almost universally employ some sort of a calibration curve that relates analyte concentration within a sample having a known analyte concentration against the signal generated by the reaction monitoring means in response to the presence of the analyte. Such samples are frequently called "calibrators" or "calibration solutions" or "standard solutions". For greatest accuracy, calibration curves are established at regular intervals, to compensate for reagent particulars, on individual analyzers, to compensate for equipment performance. The range of analyte concentrations used in establishing a full calibration curve is typically chosen to extend below and beyond the range of analyte concentrations expected to be found within biological samples like blood, serum, plasma, urine and the like.

It is regular practice within the biochemical analytical industry to establish a full calibration curve for a chemical analyzer by using multiple calibration solutions or calibrators which have been carefully prepared with known, predetermined concentrations of analyte. These calibration or standard solutions are assayed one or more times and the mean resulting reaction signals are plotted versus their respective known analyte concentrations. A continuous calibration curve is then produced using any of several mathematical techniques chosen to produce an accurate replication of the relationship between a reaction signal and the analyte concentration. The shape of the calibration curve is affected by a complex interaction between reagents, analyte and the analyzer's electromechanical design. Thus, even if the theoretical analyte-reagent reaction is known, it is generally necessary to employ mathematical techniques to obtain an acceptable calibration curve.

One of the most widely used techniques to establish a calibration curve is the use of regression analysis, either linear or nonlinear depending on the curve shape. This is particularly true with competitive or sandwich immunoassays which frequently use nonlinear regression analysis to fit calibration data with a general nonlinear model known as the logit or Rodbard function.

A well known drawback in regression analysis, however, is that it can give biased results in analytical systems where the measurement signal variability changes with analyte concentration, such as typically found with immunoassays. This is a particular problem for systems which have greater inherent variability at the high end of the calibration curve while the most clinically important region is at the low end of the calibration curve (e.g., TSH, HCG, CKMB, etc.). In these cases standard regression analysis will preferentially fit the high end calibrators at the expense of the low end and potentially introduce significant bias in the low end region.

Since the accuracy with which the calibration curve is established directly affects the accuracy of an assay made on clinical samples, a solution to the problem is to use weighted regression analysis. In this case, the fit is artificially forced or "weighted" to focus on the portion of the calibration curve that corresponds to the range of greatest clinical significance for the analyte of interest. This is particularly critical for high sensitivity immunoassays, which are capable of detecting very low levels of analyte. In these instances, a high weighting factor is applied to the calibrator solutions that have the lowest analyte concentrations, which are frequently the most precise and clinically relevant, so that the resultant full calibration curve is forced to most accurately model the lower range of reaction signals, albeit at the expense of potentially allowing some bias at higher analyte concentrations.

A popular practice is to incorporate a weighting scheme into the software that controls the operation of the analyzer so that technicians performing the calibration and operating the analyzer are not required to also perform the mathematical calculations. However, this convenience does not exist within all analyzers, in particular within older analyzers designed before such high sensitivity immunoassays were commercially available. For this reason, a simple method for calibrating analyzers without resorting to complex weighting techniques is needed to achieve increased calibration curve accuracy with high sensitivity immunoassays.

U.S. Pat. No. 3,960,497 discloses the basic concepts of calibrating and verifying the calibration of a chemical analyzer using standard solutions having known values of the particular characteristic being measured.

U.S. Pat. No. 4,043,756 discloses a method to provide in an automatic chemical testing apparatus means for providing calibration values to processing circuitry, and selecting one of a plurality of calibration signal values for use as the calibration value based on comparison with suitable values resulting from use of the signal as a calibration value.

U.S. Pat. No. 4,169,125 is a method for calculating calibration curve fit values for a polynomial regression curve equation followed by a Newton-Raphson inversion on the equation. This is illustrative of the sophistication often employed in achieving calibration of a chemical analysis system.

U.S. Pat. No. 5,083,283 discloses a method for obtaining a calibration curve using a least-squares approach in which a portion of the measured data are weighted near a limit value used in deciding the components of a living organism.

U.S. Pat. No. 5,281,540 discloses a conventional least-squares regression technique to obtain the parameters and type of curve fit for different lots of analytical reagents.

U.S. Pat. No. 5,348,889 provides a calibration curve plotting the interrelation between the calibration values of a small number of different known standard solutions and their measured reaction signals, the calibration curve being modified by extrapolating an imaginal point. The calibration value of the imaginal point includes both the upper limit of the measurement range and a zero value point.

U.S. Pat. No. 5,554,539 discloses a method for recalibrating a calibration curve by determining ratios between actual and expected reaction signals at lower and higher concentrations. The ratios are then used in combination with pseudo-signals correspondingly lower and higher than the calibration range to obtain an extended calibration curve range.

U.S. Pat. No. 5,795,791 discloses a calibration curve obtained by splitting an original logistic calibration curve into three parts, a low concentration region represented by a multi-degree function, an intermediate concentration region represented by an exponential degree function, and a high concentration region represented by another multi-degree function to produce a three-part calibration curve that has identical slopes at the boundary between them.

Accordingly, from a study of the different approaches taken in the prior art to the problems presented by the necessity for providing calibration curves in high sensitivity immunoassays, there remains a need for a method to produce a calibration curve having increased accuracy at low analyte concentrations without introducing complex weighting calculations and without unduly adding to the number of calibration standard solutions in the low end region of interest.

BRIEF SUMMARY OF THE INVENTION

Many of these disadvantages within the prior art are overcome by using the apparatus and methods of this invention. For the assays of interest, the lowest signal portions of reaction curves are most critical in diagnostic analysis. A method has been discovered that consists of essentially inverting the standard curve obtained with calibration solutions before applying a logit transformation to determine an appropriate calibration curve. This invention assigns higher transformed signal values to the lower concentration regions of the calibration curve and lower transformed signal values to the higher concentration regions of the calibration curve, which are of less diagnostic interest. Increased calibration accuracy is thereby obtained in the regions of greatest diagnostic interest without otherwise requiring weighting factors to be introduced.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

An exemplary measuring means useful in performing this invention employs a spectrophotometer to measure a turbidity or absorbance signal in an immunoassay to measure the concentration or presence of a wide variety of bacteria, cell-surface antigens, serum proteins or other analytes of clinical interest. Biochemical immunoassays in general depend upon a mathematical equation that accurately replicates a curve generated by analyzing a series of calibrator solutions to provide a relationship between analyzer signal and concentration of the moiety of interest. A curve fit routine optimizes a mathematical equation to the calibration curve data. From this mathematical equation, any subsequent measured reaction signal can be interpolated and a resultant analyte concentration provided to an operator.

In most curve fit optimization processes, the best curve fit is obtained by a least-square regression algorithm which minimizes the squared difference between the raw signal and the calculated signal from the target equation. The resulting equation is therefore naturally weighted or biased in favor of the part of the calibration curve with the largest signal. This bias can be even more apparent in systems where the inherent variability of the signal response increases at larger analyte concentrations, such as in many immunoassays.

In many instances however, the low-end region of the curve contains significant performance characteristics for the assay. These might include sensitivity, precision, accuracy, and critical medical decision levels. In other instances, this region of the curve may also contain significant curve characteristics that might be ignored by a normal calibration routine. For example, in a prealbumin assay, varying polyclonal affinities and heterogeneity found in various reagent lots may show small but significant deviation from a normal fit in the clinically significant, low end region of the calibration curve.

Figure 1:
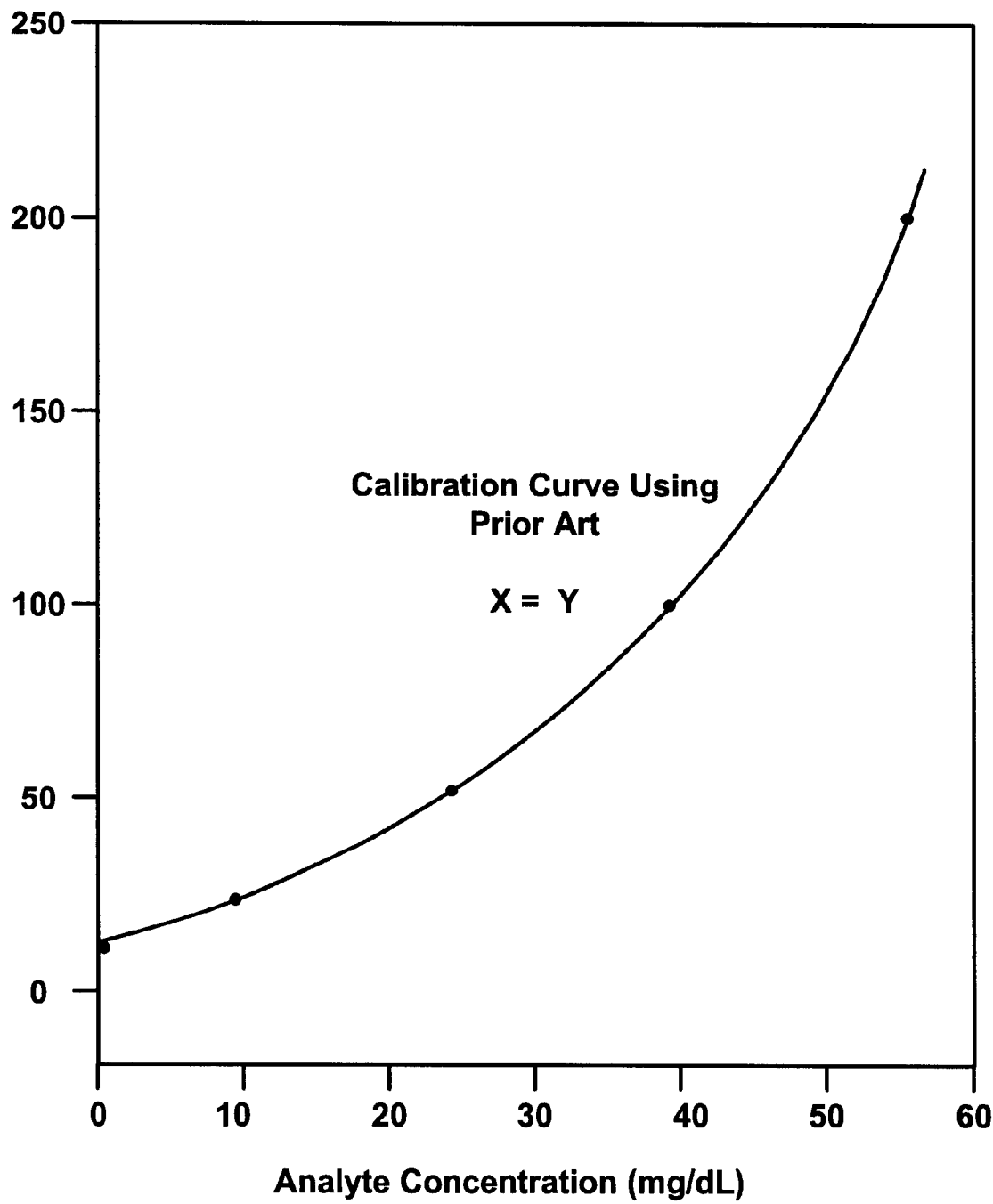
FIG. 1 is a prior art calibration curve which correlates spectrophotometric absorbance rate signal to analyte concentration.

FIG. 1 shows a conventional calibration curve that may be produced using a chemical analyzer to provide actual analyzer measurements of the amount of analyte contained in a number of standard solutions prepared with accurately known analyte concentrations. Typically, standard solution, having a range of concentrations that cover the clinical range of interest are used to produce such a curve.

Figure 2:
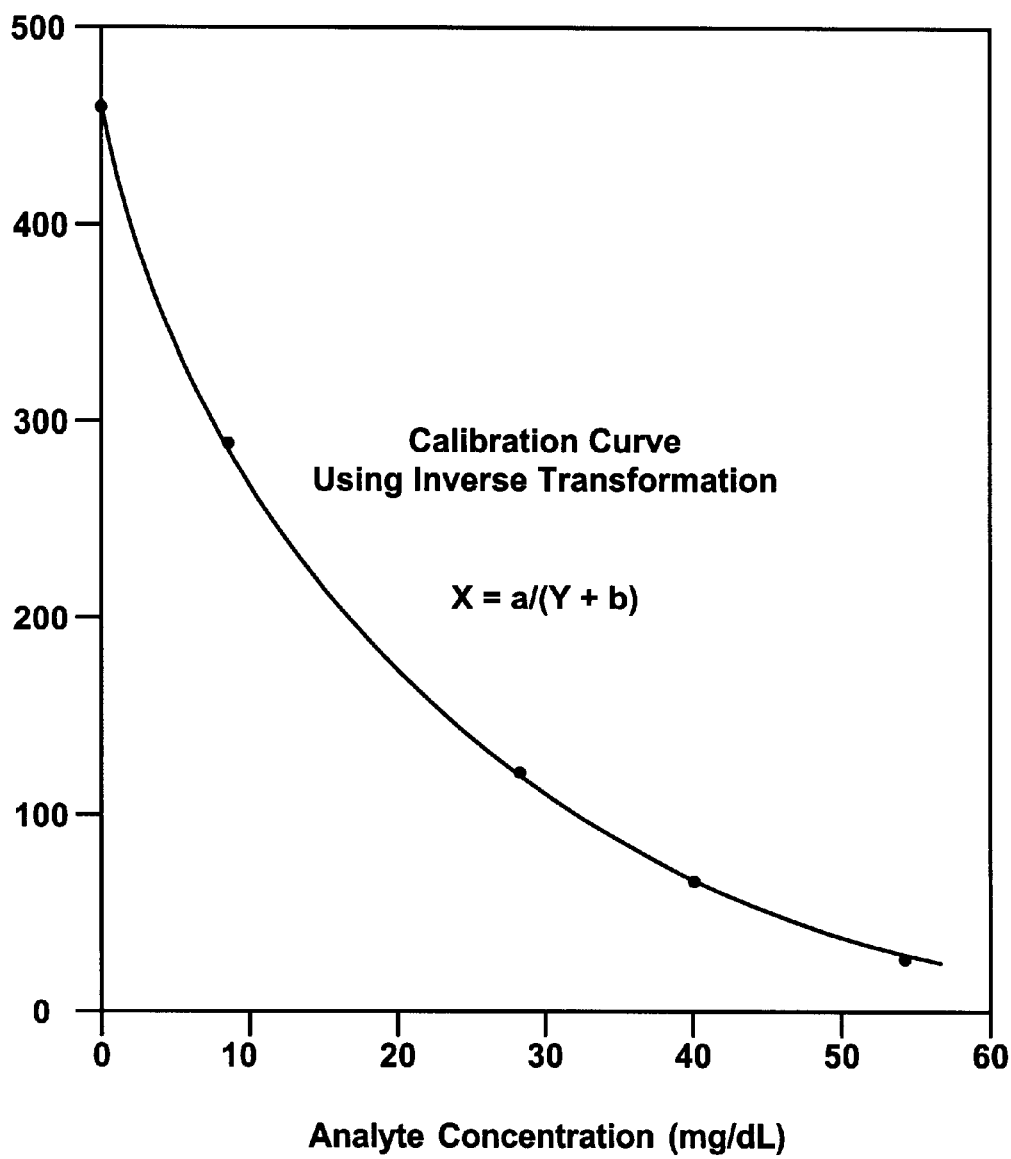
FIG. 2 is a calibration curve generated using an Inverse Transformation of the present invention prior to making a logit transformation.
Figure 3:
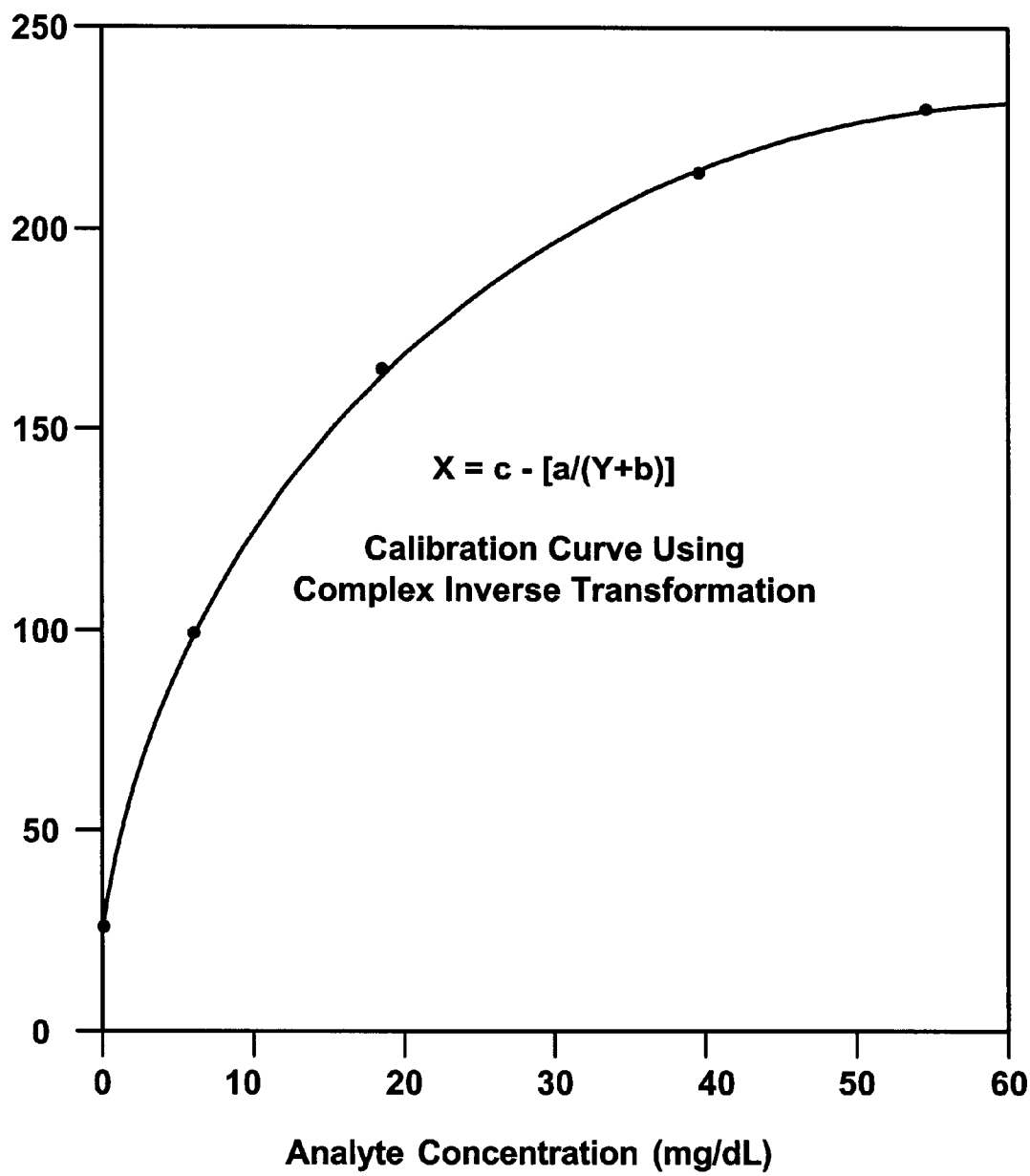
FIG. 3 is a calibration curve generated using a Complex Transformation of the present invention prior to making a logit transformation.

The present invention differs from the prior art by expanding the low end of a positive calibration curve (wherein signal increases are found at increasing analyte concentrations) by a mathematical transformation which forces the normal curve fit routine to provide special focus at the low end without utilization of a weighting program, which may not be available for certain instrument types. Two general forms of mathematical transformation are described by the present invention. FIG. 2 is an example of an Inverse Transformation, where the resultant calibration standard curve has also been inverted from a positive to a negative calibration curve (wherein signal decreases are found at increasing analyte concentrations). FIG. 3 is an example of a Complex Inverse transformation. In the latter case, the resultant curve is still a positive calibration curve, except for the enhanced curvature and separation at the key portion of the curve where improved accuracy enables increased diagnostic accuracy.

The present invention improves the curve fit at the low analyte concentration region of a calibration curve where reaction signal obtained with reaction monitoring means is usually very small and a normal regression curve fit routine is unable to provide the desired degree of accuracy. Various types of polyclonal antibodies and potentially conjugates may also exhibit poor curve shape at the low end due to varying antibody affinities, heterogeneities, and activities. The present invention provides accurate low-end calibration curve matching despite these types of curve shape variations.

The present invention may be applied for either positive or negative calibration curves. For a positive calibration curve, two type of transformation formula may be used: an Inverse transformation, as shown in FIG. 2, and a Complex Inverse transformation, as shown in FIG. 3. Both types of transformation equations will be described and examples shown below. In an alternate embodiment, this invention may be used with negative, inhibition type, calibration curves if increased accuracy is needed at the high-end where the reaction signal is normally very low. For negative calibration curves, both Inverse and Complex Inverse transformations may also be applied with similar but reversed resultant standard curves. These curves are not shown specifically, but will have shapes similar to FIG. 2 and FIG. 3, respectively.

Inverse Transformation Method

The Inverse Transformation Method of the present invention is a non-weighted signal transformation shown in Equation 1 below:

$$x = a/(y+b) \qquad \text{Equation 1}$$

where
- x=transformed signal
- y=measured raw signal
- a=constant which controls amplitude
- b=constant which controls curvature by which the low end of the curve is expanded and the normal curve fit routine is forced to effectively weight the low end of the standard curve without the use of a special weighting routine. Since weighting is a feature only available in the most modern instruments, the present invention allows older clinical instruments to run methods needing this special consideration.

Complex Inverse Transformation Method

In an alternate embodiment of this invention, known as the Complex Inverse Transformation process, Equation 1 is modified to include a factor that controls location of transformed signal on its axis, resulting in Equation 2 below:

$$x = c + a/(y+b) \qquad \text{Equation 2.}$$

where
- x=transformed signal
- y=measured raw signal
- a=constant which controls amplitude
- b=constant which controls curvature
- c=constant which controls location of transformed signal on its axis.

The c-term essentially modifies the location of the new standard curve on the transformed signal axis. By using a negatively valued a-term with an optimized c-term, the transformed standard curve may be made similar to the non-transformed standard curve. The only difference is the curvature at the low end of the standard curve where a larger signal to analyte slope is now available resulting in enhanced accuracy.

EXAMPLE 1

Prealbumin

Prealbumin, also known as transthyretin, is a transport protein for thyroxine (T4) and vitamin A having a molecular weight of about 55,000 Daltons. Prealbumin is synthesized by the liver, exists as a stable tetramer composed of four identical subunits, and circulates as a complex with retinol-binding protein (RBP) in a 1:1 molar ratio. Because of prealbumin's short half-life (2 days) and rapid response to lowered energy intake or nutritional repletion, prealbumin has been reported to be clinically useful in the assessment and monitoring of nutritional status. Normal concentrations of prealbumin range from about 18–37 mg/dL. In cases of moderate and severe nutritional deficiency, prealbumin concentrations range from about 11–17 mg/dL and <11 mg/dL, respectively. Accurate quantification at these low analyte concentrations is important in the initial diagnosis of nutritional deficiency and accurate monitoring of nutritional repletion evidenced by a steady increase in prealbumin concentration over time. An assay for the determination of human prealbumin in serum and plasma may be based on latex particle based turbidimetric agglutination techniques, as described in U.S. Pat. Nos.: 4,480,042 and 4,401,765. In this assay, a specific antibody-coupled particle reagent is synthesized to bind human prealbumin, agglutinate, and generate a turbidimetric signal read by a spectrophotometer. Preparation of the prealbumin particle reagent typically consists of coupling polyclonal prealbumin antibodies to latex particles by adding a sufficient quantity of antibodies selected to produce a standard curve over the assay range without evidence of antigen excess (i.e. "hook" effect). This may include the addition of free antibodies to the particle reagent to obtain a standard curve shape which minimizes analyte residual values after being linearized by a subsequent mathematical transformation. Normalization techniques to provide accurate and stable signals include: bichromatic normalization, background blanking, rate measurement, and various signals for system ultrasonic and reagent transfer errors.

Standard curves showing the correlation between sample concentrations and agglutination assay measurements for prealbumin, an exemplary use of the present invention in an assay having a positive standard curve, are compared in Table 1 below for actual signal values, and for values calculated by the Inverse Transformation and Complex Transformation standard curves of the present invention. Actual Signal Values are the measured signals produced typically by a spectrophotometer in milliabsorbance units (mA). The Inverse Transformation and Complex Transformation standard curve values represent the actual, untreated, raw signal output values modified via Equation 1 (with parameter values a=10,000 and b=20) or Equation 2 (with parameter values a=–10,000, b=20, and c=500) to result in the Inverse Transformation or the Complex Transformation standard curves, respectively, of the present invention.

TABLE 1

Prealbumin standard curves for Actual Signal and Inverse and Complex Transformation

| Sample Value (mg/dL) | Actual Signal Value (mA) | Inverse Transformation (Equation 1) | Complex Transformation (Equation 2) |
|---|---|---|---|
| 0.0 | 0.4 | 490.2 | 6.1 |
| 10.2 | 16.0 | 278.2 | 117.4 |
| 25.4 | 51.5 | 139.9 | 212.3 |
| 40.1 | 105.8 | 79.5 | 261.4 |
| 55.3 | 199.8 | 45.5 | 291.5 |

When a calibration curve is generated from spectrophotometer signals and known concentrations of calibrator samples, errors within the curve-fitting process may be determined by measuring deviation of the curve-fit values for each calibration solution from its known analyte concentrations, a deviation that is known as the analyte residual value. Analyte residual values for a 0 mg/dL calibrator are given in analyte concentration units, mg/dL. Analyte residual values for other calibrators are given in percent units relative to their respective known concentration values. The analyte residual results for the three standard curves in Table 1 are shown in Table 2, below.

TABLE 2

Prealbumin Analyte Residual Values for Actual Signal and Inverse and Complex Transformation

| Analyte Value (mg/dL) | Actual Signal Value | Inverse Transformation | Complex Transformation |
|---|---|---|---|
| 0.0 | 0.975 (mg/dL) | 0.000 (mg/dL) | 0.000 (mg/dL) |
| 10.2 | −4.41% | 0.00% | 0.00% |
| 25.4 | −1.81% | −0.01% | 0.01% |
| 40.1 | 0.84% | 0.01% | −0.01% |
| 55.3 | −0.12% | −0.01% | 0.01% |

The residuals for the raw Actual Signal standard curve show greater deviation as the analyte concentration and the reaction signal decrease. However, these same data, when transformed by either the Inverse Transformation or the Complex Transformation resulted in standard curves show dramatic improvements in low-end accuracy.

Furthermore, the prealbumin residual for the middle and high end of the curves also showed marked improvement. Typically, by controlling the various constants in Equations 1 or 2, the curve-fitting error (residual analyte %) may be adjusted and balanced to spread across the standard curve. Depending on the particular assay needs, various segments of the standard curve could then be given lower or higher percent residual as necessary.

One of the disadvantages of using polyclonal antibodies in an assay like the prealbumin assay, is that various low-end curve shapes exist within the assay due to the presence of antibodies having various antibody affinity and avidity. By using the improved transformation methodology of the present invention, more emphasis is given to the low-end of the prealbumin calibration curve for the curve-fitting algorithm. The result is better accuracy at the low-end of the calibration curve. Thus, a larger variety of polyclonal antibodies may be used in the assay with minimal or no impact on the assay accuracy. Such advantage, may also be extended to monoclonal antibodies if they were used in performing the assay.

During commercial production of prealbumin assay reagents, a linear optimization of the antibody-reagent is necessary to provide an optimum calibration curve. One of the major criteria used in this determination is residuals at the various calibrator levels. In the prealbumin linear optimization example shown in Table 3A, various concentrations in mg/mL of the antibody-reagent were tested using a curve fit based on the raw signal, as would be done in the prior art. The optimal antibody-reagent concentrations may be chosen based on minimum residuals at a specific area or across the whole assay range, depending on the need of the specific assay. In this example, analyte residuals from curve fitting based on the raw signal linear are given in Table 3C. Antibody-reagent concentrations of 0.21 and 0.24 mg/mL are eliminated due to percent residuals higher than 5% at calibrator level 2, 7.1% and 6.0% respectively. Based on calibrator level 1, a 0.30 mg/mL reagent concentration would be chosen as optimum since it exhibits the lowest residual of −0.61.

When the Inverse Transformation is applied to the raw signal using Equation 1 with transform constants a=10,000 and b=20, the resultant standard curves are shown in Table 3B. The marked improvement in residuals for the low-end of all the curves is still evident, as shown in Table 3D. More importantly, all five levels of the reagent concentrations may be used with all the residuals being below the 5% control limit. Although the 0.27 mg/mL concentration shows the lowest residual across the entire assay range, lower reagent concentrations may be chosen without the assay being out-of-limit. From a manufacturing perspective, several advantages become evident. Several concentration levels, which previously were unacceptable, may now be used and lower concentration levels result in a reduced cost of the reagent. An increased breadth of acceptable concentrations also indicate a much more robust reagent system, where more concentration variations may be allowed for in the manufacturing process without loss of assay quality.

TABLE 3A

Prealbumin Assay Reagent Optimization using Actual Signal Process.

| Analyte Value | Particle/Antibody Concentration (mg/mL) | | | | |
|---|---|---|---|---|---|
| (mg/dL) | 0.210 | 0.240 | 0.270 | 0.300 | 0.330 |
| 0.0 | 0.4 | 0.5 | 0.4 | 0.1 | −0.5 |
| 10.2 | 21.1 | 18.3 | 16.0 | 14.4 | 13.2 |
| 25.4 | 61.3 | 56.3 | 51.5 | 47.8 | 43.9 |
| 40.1 | 142.5 | 121.4 | 105.8 | 94.4 | 83.6 |
| 55.3 | 245.0 | 225.8 | 199.8 | 173.5 | 155.6 |

TABLE 3B

Prealbumin Assay Reagent Optimization using Inverse Transformation Process.

| Analyte Value | Particle/Antibody Concentration (mg/mL) | | | | |
|---|---|---|---|---|---|
| (mg/dL) | 0.210 | 0.240 | 0.270 | 0.300 | 0.330 |
| 0.0 | 490.2 | 488.0 | 490.2 | 496.9 | 512.3 |
| 10.2 | 243.3 | 261.1 | 278.2 | 290.7 | 301.2 |
| 25.4 | 123.0 | 131.1 | 139.9 | 147.5 | 156.5 |
| 40.1 | 61.5 | 70.7 | 79.5 | 87.4 | 96.5 |
| 55.3 | 37.7 | 40.7 | 45.5 | 51.7 | 56.9 |

TABLE 3C

Prealbumin Analyte Residual Values for Actual Signal in Reagent Optimization

| Analyte Residual Value | Particle/Antibody Concentration (mg/mL) | | | | |
|---|---|---|---|---|---|
| (mg/dL) | 0.210 | 0.240 | 0.270 | 0.300 | 0.330 |
| 0.0 | 0.13 | −.056 | −0.85 | −0.61 | −1.24 |
| 10.2 | 7.1% | 6.0% | 3.8% | 1.3% | 3.2% |
| 25.4 | −4.9% | −0.6% | 1.7% | 2.3% | 3.9% |
| 40.1 | 1.7% | −0.0% | −0.8% | −1.0% | −1.7% |
| 55.3 | −0.3% | 0.0% | 0.1% | 0.2% | 0.3% |

TABLE 3D

Prealbumin Analyte Residual Values
For Inverse Transformation in Reagent Optimization

| Analyte Residual Value | Particle/Antibody Concentration (mg/mL) | | | | |
|---|---|---|---|---|---|
| (mg/dL) | 0.210 | 0.240 | 0.270 | 0.300 | 0.330 |
| 0.0 | −0.001 | −0.001 | 0.000 | 0.001 | 0.002 |
| 10.2 | 0.5% | 0.2% | 0.0% | −0.1% | −0.3% |
| 25.4 | −2.5% | −1.0% | −0.0% | 0.5% | 1.0% |
| 40.1 | 4.9% | 1.8% | 0.01% | −0.9% | −1.8% |
| 55.3 | −2.7% | −1.0% | −0.0% | 0.6% | 1.1% |

EXAMPLE 2

IgA

An IgA assay is a protein agglutination immunoassay for the determination of Immunoglobulin A in human serum and plasma. For this method, a polyclonal antibody reagent is used to bind human IgA and induce agglutination that generates a turbidimetric signal on a spectrophotometer; such an assay is another exemplary use of the present invention in an assay having a positive standard curve. Such an antisera agglutination technique is well established in the literature and is used in commercially available clinical analyzers. During the IgA assay, a first sample test well may be used for sample predilution and as a source of analyte for excess antigen testing wherein sample is added in two steps: a first addition of a small portion, for example, about 10%, of the total volume and a later addition of the remaining larger portion of the total volume. Signal readings are taken after each addition and compared with each other to indicate atypical reactions, such as antigen excess. Normalization techniques to provide accurate and stable signals include: bichromatic normalization, background blanking, rate measurement, and various high wavelength flags for system ultrasonic and reagent transfer errors.

Standard curves showing the turbidimetric signal generated by IgA calibrators of known concentration are shown in Table 4A for three types of data output, in a manner similar to those of the prealbumin assay of Example 1. Data in the Actual Signal Value column represent untreated or raw signals from the analyzer. The third column contains the results of modifying the actual signals using Equation 1 to produce an Inverse Transformation standard curve, using transform constants a=100,000 and b=30, of the present invention. The fourth column contains the results of modifying the actual signals using Equation 2 to produce a Complex Transformation standard curve, using transform constants a=−100,000, b=30, and c=1880 of the present invention.

TABLE 4A

IgA Standard Curves for Actual Signal
Inverse Transformation and Complex Transformation

| Sample Value (mg/dL) | Actual Signal Value (mA) | Inverse Transformation (Equation 1) | Complex Transformation (Equation 2) |
|---|---|---|---|
| 3.0 | 25.5 | 1801.1 | 78.2 |
| 90.0 | 40.6 | 1416.4 | 463.6 |
| 281.0 | 71.5 | 985.7 | 894.3 |

TABLE 4A-continued

IgA Standard Curves for Actual Signal
Inverse Transformation and Complex Transformation

| Sample Value (mg/dL) | Actual Signal Value (mA) | Inverse Transformation (Equation 1) | Complex Transformation (Equation 2) |
|---|---|---|---|
| 560.0 | 106.0 | 735.4 | 1144.6 |
| 1074.0 | 159.0 | 529.2 | 1350.8 |

In order to evaluate the accuracy of using standard curves for the three types of data shown in Table 4A, analyte residual values were determined, as shown in Table 4B. Residual values for the actual-signal standard curve show greater deviation at lower analyte concentrations. However, when the analyzer signals are transformed by the Inverse or the Complex Transformation processes, marked improvements in accuracy are seen in the lower range of analyte concentrations. At the high-end of the standard curves, slightly higher residuals are observed. However, these are all within the acceptable limit of 5%.

TABLE 4B

IgA Residual Analyte Values for Actual Signal,
Inverse Transformation and Complex Transformation

| Sample Value (mg/dL) | Actual Signal Value | Inverse Transformation | Complex Transformation |
|---|---|---|---|
| 3.0 | −14.5% | −4.7% | 4.6% |
| 90.0 | −1.5% | 1.1% | −1.0% |
| 281.0 | 2.3% | −1.7% | 1.7% |
| 560.0 | −1.2% | 1.9% | −1.9% |
| 1074.0 | 0.2% | −0.9% | 1.0% |

In order to evaluate results from the improved standard or calibration curves using the Complex Transformation (Equation 2), various levels of antibody titer were tested in an IgA immunoassay. Raw signal linear optimizations are shown in Table 5A. When the Complex transformation is applied to the untreated analyzer signals, the resultant Complex Transformation standard curves of the present invention are shown in Table 5B.

TABLE 5A

IgA Assay Reagent Optimization
using Prior Art Process.

| Analyte Value (mg/dL) | Antibody Reagent Titer (mg/dL) | | | | |
|---|---|---|---|---|---|
| | 1.20 | 1.35 | 1.50 | 1.65 | 1.80 |
| 3.0 | 20.2 | 22.8 | 23.5 | 25.5 | 27.5 |
| 90.0 | 34.0 | 36.6 | 39.5 | 40.6 | 43.0 |
| 281.0 | 62.7 | 66.4 | 68.9 | 71.5 | 90.3 |
| 560.0 | 95.3 | 99.7 | 102.9 | 106.0 | 109.7 |
| 1074.0 | 141.2 | 148.8 | 155.3 | 159.0 | 164.7 |

TABLE 5B

IgA Assay Reagent Optimization using Complex Transformed Process.

| Analyte Value | Antibody Reagent Titer (mg/mL) | | | | |
|---|---|---|---|---|---|
| (mg/dL) | 1.20 | 1.35 | 1.50 | 1.65 | 1.80 |
| 3.0 | −112.0 | −13.9 | 9.1 | 78.2 | 140.9 |
| 90.0 | 317.5 | 378.5 | 441.2 | 463.6 | 510.1 |
| 281.0 | 801.3 | 842.7 | 868.9 | 894.3 | 1048.7 |
| 560.0 | 1081.9 | 1109.0 | 1127.6 | 1144.6 | 1163.9 |
| 1074.0 | 1295.9 | 132.7 | 1340.3 | 1350.8 | 1366.4 |

In order to evaluate the accuracy of using standard curves as shown in Tables 5A and 5B, analyte residual values were determined and compared to the untreated signal standard curves as shown in Tables 5C and 5D. In the prior art reagent optimization example, titer of 1.80 mg/mL may be eliminated due to poor residuals across the entire standard curve. Although the residual at calibrator level 1 of 3 mg/dL is higher than desired, optimum titer chosen would be the 1.65 mg/mL due to the minimum residuals for calibrator levels 1 and 2 at this titer. Using the Complex Transformation process of the present invention, marked improvement in residuals for calibrator levels 1 and 2 is found in all the titers tested. Although the 1.50 mg/mL titer does show the lowest residual across the entire assay range, a titer of 1.20 mg/mL may be chosen without the assay being out-of-limit. Thus, several titer levels, which previously were unacceptable, may now be used without loss of accuracy. Application of the present invention in an IgA assay may thereby provide reduced reagent cost and a more robust reagent system, where more variation in the titers may be allowed for in a reagent manufacturing process with minimal loss of assay quality.

TABLE 5C

IgA Residual Analyte Values for Prior Art in Reagent Optimization

| Residual Analyte Value | Antibody Reagent Titer (mg/mL) | | | | |
|---|---|---|---|---|---|
| (% mg/dL) | 1.20 | 1.35 | 1.50 | 1.65 | 1.80 |
| 3.0 | 53.5% | 56.6% | −100.7% | −14.5% | 97.5% |
| 90.0 | −3.6% | −4.5% | 3.4% | −1.6% | −20.7% |
| 281.0 | 0.9% | 1.7% | 1.8% | 2.3% | 21.3% |
| 560.0 | −0.2% | −0.7% | −1.5% | −1.2% | −12.4% |
| 1074.0 | 0.0% | 0.1% | 0.3% | 0.2% | 3.1% |

TABLE 5D

IgA Residual Analyte Values For Complex Transformed Process

| Residual Analyte Value (% mg/dL) | Antibody Reagent Titer (mg/mL) | | | | |
|---|---|---|---|---|---|
| % mg/dL | 1.20 | 1.35 | 1.50 | 1.65 | 1.80 |
| 3.0 | 3.3% | 5.9% | 1.2% | −4.6% | 4 1.4% |
| 90.0 | −0.7% | −1.2% | −0.4% | −1.0% | −5.8% |

TABLE 5D-continued

IgA Residual Analyte Values For Complex Transformed Process

| Residual Analyte Value (% mg/dL) | Antibody Reagent Titer (mg/mL) | | | | |
|---|---|---|---|---|---|
| % mg/dL | 1.20 | 1.35 | 1.50 | 1.65 | 1.80 |
| 281.0 | 1.1% | 1.8% | 0.7% | 1.7% | 12.7% |
| 560.0 | −1.4% | −2.1% | −0.8% | −1.9% | −20.9% |
| 1074.0 | 0.8% | 1.2% | 0.4% | 1.0% | 45.5% |

EXAMPLE 3

IgG and IgM

IgG and IgM assays are protein agglutination immunoassays for the determination of plasma Immunoglobulin G, IgG, and Immunoglobulin M, IgM, in human serum, respectively. For these methods, additional exemplary uses of the present invention in an assay having a positive standard curve, similar agglutination techniques as with IgA are used to generate a turbidimetric signal calibration curves and analyte residuals comparisons were made between prior art and either the Inverse or Complex transformation results.

In these instances, Equation 1 was used to produce an Inverse Transformation standard curve for IgG, using transform constants a=100,000 and b=40, of the present invention, and Equation 2 was used to produce a Complex Transformation standard curve, using transform constants a=−100,000, b=40, and c=1330. When the Complex Transformation of Equation 2 is applied to the raw signal, marked improvement in IgG residuals for calibrator levels 1 and 2 was found across a full range of titers.

Equation 1 was also used to produce an Inverse Transformation standard curve for IgM, using transform constants a=100,000 and b=30, of the present invention, and Equation 2 was used to produce a Complex Transformation standard curve, using transform constants a=−100,000, b=40, and c=2280. When the Complex Transformation of Equation 2 is applied to the raw signal, marked improvement in IgM residuals for calibrator levels 1 and 2 was found across a full range of titers.

EXAMPLE 4

Valproic Acid

The present invention may also be used in a latex agglutination assay for the determination of serum and plasma anticonvulsant therapeutic drug Valproic Acid. For this method, specific particle and antibody reagents are prepared to agglutinate and generate a signal indicative of the amount of turbidimetric agglutination typically measured using a spectrophotometer. The presence of the therapeutic drug in the patient sample will compete for the binding sites available in the reaction and inhibit the agglutination. The result is a negative standard curve where increasing analyte concentration yields a decrease in the turbidimetric signal; a valproic acid assay is an exemplary use of the present invention in an assay having a negative standard curve.

Normalization techniques to provide accurate and stable signals include: bichromatic normalization, background blanking, rate measurement, and various high signals for system ultrasonic and reagent transfer errors.

Standard curves generated from calibrator solutions with known concentrations of valproic acid are shown in Table 6 with actual signal values and for values calculated by Equation 1 using transformation constants a=100,000 and b=25 and for the Inverse Transformation and for the Complex Inverse Transformation of Equation 2 and using transformation constants a=−100,000, b=25 and c=900. The negative standard curve may be seen in the Inverse relationship between calibrator concentration versus actual signals. In this further embodiment of the present invention, the Inverse transformation of a negative standard curve is a positive standard curve. It can be seen that the Complex Inverse Transformation of a negative standard curve provides a resultant positive standard curve, an exemplary use of the present invention in an assay having a negative standard curve that is effectively changed into a positive standard curve when using Equation 2.

TABLE 6

Valproic Acid Standard Curves for Actual Signal and Inverse and Complex Inverse Transformation

| Sample Value (mg/mL) | Actual Signal Value (mA) | Inverse Transformation (Equation 1) | Complex Transformation (Equation 2) |
| --- | --- | --- | --- |
| 0.0 | 381.9 | 245.8 | 654.2 |
| 17.1 | 316.5 | 292.8 | 607.2 |
| 36.7 | 262.1 | 348.3 | 551.7 |
| 72.5 | 178.1 | 492.4 | 407.6 |
| 154.9 | 87.5 | 888.9 | 11.1 |

As described hereinbefore, when a calibration curve is generated from spectrophotometer signals and curve-fitted to the known concentrations of calibrator samples, errors within the curve-fitting process may be quantified in terms of the analyte residual value for each calibrator sample. The analyte residual result for the three valproic acid standard curves of Table 6 are shown in Table 7, below.

TABLE 7

Valproic Acid Analyte Residual Values for Actual Signal and Inverse and Complex Inverse Transformation

| Analyte Value (ug/mL) | Actual Signal Value | Inverse Transformation | Complex Transformation |
| --- | --- | --- | --- |
| 0.0 | 0.2 ug/mL | 0.56 ug/mL | 0.57 ug/mL |
| 17.1 | −4.4% | −6.4% | −6.4% |
| 36.7 | 3.1% | 1.8% | 1.8% |
| 72.5 | −1.3% | −0.2% | −0.2% |
| 154.9 | 0.3% | 0.0% | 0.0% |

The residuals for the raw signal, prior art, standard curve exhibit increased amplitude in ug/mL as the analyte concentration increases and the reaction signal decreases. However, this same data, when transformed by the Inverse or the Complex processes resulted in standard curves with marked improvement in middle and high-end accuracy, calibrator levels above 36.7 ug/mL. Slightly higher residuals resulted for the low-end of the transformed curves, calibrator levels 0.0 and 17.1 ug/mL. However, these are not significant due to the small increase and the lesser clinically significant portion of the standard curve for valproic acid.

EXAMPLE 5

C-reactive Protein Assay

The C-reactive protein assay, CRP, of the present invention is an agglutination immunoassay for the determination of CRP in human serum and plasma. The assay is based upon a particle/antibody reagent that is synthesized to bind human CRP, agglutinate, and generate a turbidimetic signal on a spectrophotometer. As in the prealbumin and Ig methods, techniques to provide accurate and stable signals include: bichromatic normalization, background blanking, rate measurement, and various high wavelength signals or flags to indicate system ultrasonic and reagent transfer errors.

In the instance of CRP, an improved calibration method has been discovered that consists of generating two reaction rate measuring curves, the first curve generated using a sample of higher volume and the second curve using the same sample having a smaller volume. Since the first rate decreases the limit of detection or increase assay sensitivity by measuring a sample of a higher volume, it is called sensitivity rate or SR. Because the second rate extends the upper assay range by measuring a smaller volume of the same sample, it is identified as assay range rate or AR. A mathematical relationship is established between the two curves covering a low range of sample concentrations for which both curves are linear. The relationship established in the following CRP assay example is a linear regression equation between SR and AR for the lower three calibrator levels, out of total of five levels, shown later in Table 8.

From this relationship, a reaction rate measuring curve may be extrapolated to cover sample concentrations known to contain an excess of antigen relative to an amount of capture reagent. A final combined reaction rate measuring curve may be achieved by combining the low end portion of the SR measuring curve with the higher end portion of the extrapolated reaction rate measuring curve, thus eliminating measuring inaccuracies otherwise arising from the so-called hook effect. Such a process is described in co-pending application Ser. No. 09/166,026 also assigned to the assignee of the present application. In operation, a trip point or trip reaction rate is established using AR at the junction of the low end linear portion of the SR measuring curve and the higher end portion of the extrapolated reaction rate measuring curve. If the AR measured on a patient sample is below the trip point, the low end linear portion of the SR measuring curve is used to provide analytical results. On the other hand, if AR measured on a patient sample is higher than or equal to the trip point, the extrapolated reaction rate measuring curve is used to provide analytical results.

In prior art CRP assays, a logit model is used to fit the calibration curve by non-linear regression, however, because of the limitations of the logit curve fitting, accuracy at low analyte concentrations was not satisfactory. In this example, the Complex Transformation technique of Equation 2 was used to accommodate system limitations.

The Complex Transformation equations for SR and AR were determined to be:

Complex Transformed $SR$ or $CT\text{-}SR = \frac{1}{8} \times [675 - 100,000/(SR+150)]$; and  Equation 3

Complex Transformed $AR$ or $CT\text{-}AR = \frac{1}{5} \times [500 - 100,000/(SR+200)]$;  Equation 4

To ensure a linear relationship between the CT-SR and CT-AR for the lower three levels of the calibrator containing 0.00, 2.00, and 3.89 mg/dL CRP, a logit relationship between CT-SR and CT-AR was established for samples containing from 0.00 to 6.30 mg/dL CRP using 4 different particle lots and 400 CRP determinations. Thus, for CRP concentrations between 0.00 to 6.30, with a given CT-SR, the CT-AR could be predicted using the coefficients obtained from the logit relationship. Because this predicted CT-AR is obtained from CT-SR, it is named double transformed process or TCT-SR. The logit equation used to calculate TCT-SR is as follows:

$$TCT\text{-}SR = 11.773 * \{[61.589/(CT\text{-}SR + 1.1143) - 1]^{-0.56776} - 0.0054\} \quad \text{Equation 5}$$

In this example, a calibrator is used which contains five CRP levels, 0.00, 2.00, 3.89, 12.54, and 26.57 mg/dL. Since TCT-SR is essentially the predicted CT-AR using the logit linearization between the CT-SR and CT-AR for samples with CRP concentrations from 0.00 to 6.30 mg/dL, linear regression between TCT-SR and CT-AR is warranted for those concentrations. To obtain a combined standard curve from TCT-SR and CT-AR, a linear regression equation between the two rates was obtained for calibrator levels 1 to 3:

$$TCT\text{-}SR = \text{slope} * CT\text{-}AR + \text{intercept} \quad \text{Equation 6}$$

The combined standard curve was built by plotting either straight or extrapolated TCT-SRs against CRP concentrations. For calibrator levels 1 to 3, TCT-SR is used in the combined standard curve. As for calibrator levels 4 and 5, TCT-SR used in the curve is extrapolated from Equation 6 by CT-AR. The combined curve is fitted by logit function. To measure a sample, the CT-AR for the level 3 calibrator is established to determine whether to use the straight or extrapolated TCT-SR for calculating the CRP concentration. If the CT-AR is greater than or equal to the trip point, the extrapolated TCT-SR using Equation 6 is used, otherwise, the straight TCT-SR is used.

Figure 4:
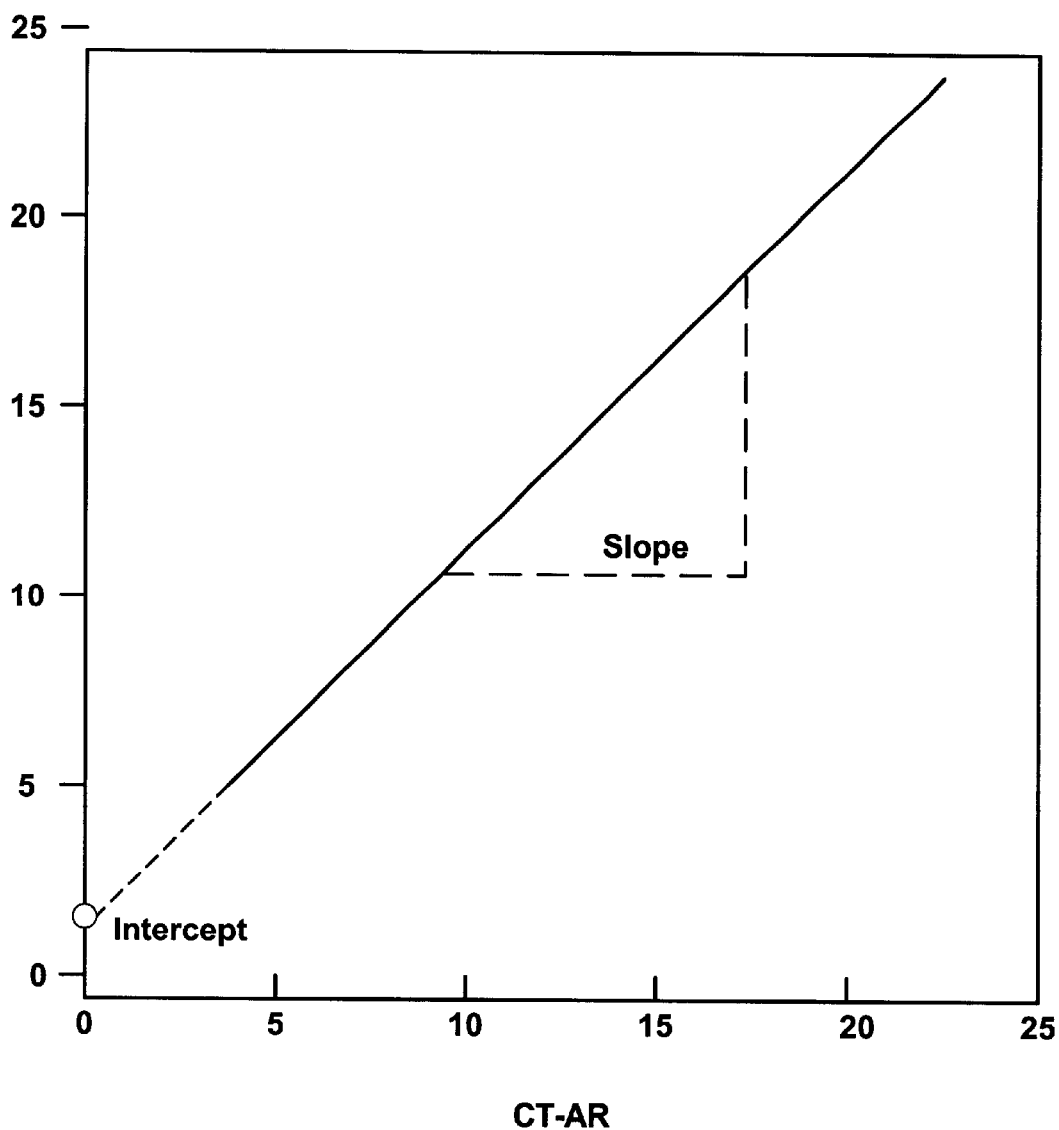
FIG. 4 shows the results of an alternate embodiment of the present invention using regression analysis for three calibrators.

FIG. 4 shows the results of a conventional linear regression analysis between the rates of the TCT-SR and CT-AR for the lower 3 levels of calibrator. The resulting slope and intercept terms are used to extrapolate the combined reaction rate (TCT-SR) for samples having an antigen level or concentration that is higher than that in Level 3.

Figure 5:
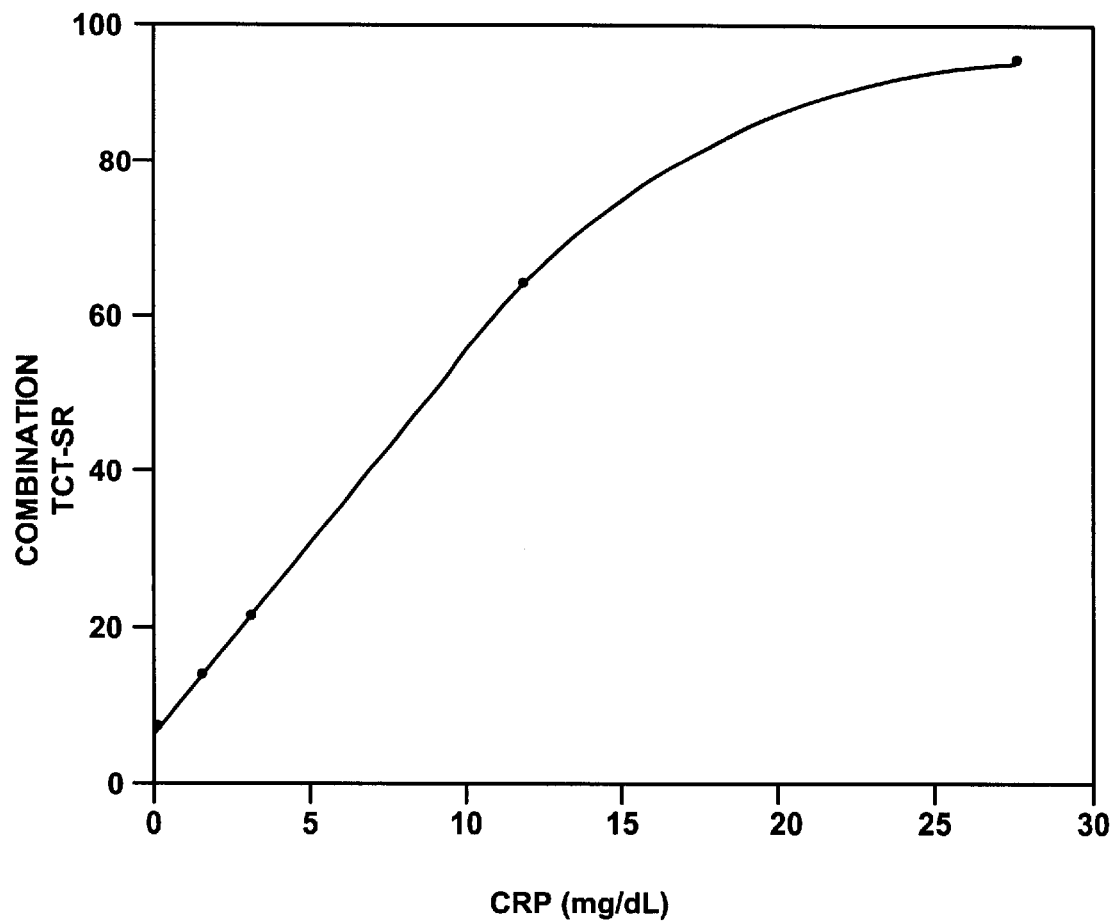
FIG. 5 is a combined reaction rate measuring for five calibrators.

FIG. 5 is a reaction rate measuring curve resulted from combining the straight TCT-SR for the lower 3 levels of calibrator and the extrapolated TCT-SR for calibrator levels 4 and 5. The combined curve is produced as seen in Table 8.

TABLE 8

| CRP (mg/L) | TCT-SR | TAR | Combined CT-SR | Comment |
|---|---|---|---|---|
| 0.0 | 2.7 | 2.4 | 2.4 | TCT-SR is used |
| 2.00 | 12.25 | 12.40 | 12.25 | TCT-SR is used |
| 3.89 | 22.98 | 23.68 | 22.98 | CT-AR is the trip point, TCT-SR is used |
| 12.54 | 38.84 | 66.38 | 64.12 | Extrapolated TCT-SR |
| 26.57 | 10.39 | 93.98 | 90.69 | Extrapolated TCT-SR |

An extrapolated TCT-SR may be calculated from CT-AR using the following equation:

$$TCT\text{-}SR = 0.223 + 0.963 * CT\text{-}AR \quad \text{Equation 7}$$

where slope and intercept are established by linear regression between TCT-SR and CT-AR shown in FIG. 4.

To generate a combined standard curve, a trip point or trip rate is established such that if CT-AR is equal to or lower than the trip point, TCT-SR may be safely used "as is", without further adjustment. However, if CT-AR is greater than the trip point, an extrapolated TCT-SR is generate by Equation 5. Straight TCT-SR may then be used along with extrapolated TCT-SR to establish a standard curve. In the above example, CT-AR at 3.89 mg/dL CRP was used as the trip point. In general, the CT-AR for the highest level used in the linear regression is the trip point.

Results from the CRP reagent linear optimization are shown in Tables 9A–9D, where various levels of the particle/antibody reagent concentrations were tested. Raw signal linear optimization is shown in Table 9A. All concentrations tested showed acceptable residual at calibrator levels from 2 to 5, except for 0.90 mg/mL. When the Complex double transformation is applied to the raw signal, the resultant standard curves are shown in Table 9B. Marked improvement in residuals for calibrator levels 1 and 2 are shown across all reagent concentrations. Residual analyte levels shown in Tables 9C and 9D reveal that calibrator level 1 reached a low error of −0.005 mg/dL at reagent concentration of 1.62 mg/mL. The double transformation utilization thereby provided better low-end accuracy across all concentrations and also provided a broader acceptable reagent concentration range when compared to use of the actual signal value calibration process.

TABLE 9A

CRP Assay Reagent Optimization using Actual Signal Process

| Analyte Value | Particle/Antibody Reagent Concentration (mg/mL) | | | | |
|---|---|---|---|---|---|
| (mg/dL) | 0.90 | 1.08 | 1.26 | 1.44 | 1.62 |
| 0.00 | 2.9 | 7.1 | 7.0 | 7.1 | 8.0 |
| 2.00 | 102.2 | 100.0 | 95.8 | 93.1 | 89.9 |
| 3.89 | 199.0 | 195.1 | 186.4 | 180.6 | 170.9 |
| 12.54 | 769.1 | 766.2 | 743.7 | 704.8 | 647.3 |
| 26.57 | 1341.0 | 1409.2 | 1384.1 | 1303.1 | 1172.5 |

TABLE 9B

CRP Assay Reagent Optimization using Complex Inverse Transformation Process

| Analyte Value | Particle/Antibody Concentration (mg/mL) | | | | |
|---|---|---|---|---|---|
| (mg/dL) | 0.90 | 1.08 | 1.26 | 1.44 | 1.62 |
| 0.0 | 2.4 | 3.2 | 3.2 | 3.2 | 3.4 |
| 2.00 | 14.2 | 14.0 | 13.5 | 13.2 | 12.9 |
| 3.89 | 26.4 | 25.8 | 24.5 | 23.6 | 22.3 |
| 12.54 | 65.5 | 66.2 | 64.3 | 61.2 | 56.5 |
| 26.57 | 85.6 | 89.5 | 88.0 | 83.9 | 77.0 |

TABLE 9C

CRP Residual Analyte Values for Actual Signal in Reagent Optimization

| Analyte Value | Particle/Antibody Concentration (mg/mL) | | | | |
|---|---|---|---|---|---|
| (mg/dL) | 0.90 | 1.08 | 1.26 | 1.44 | 1.62 |
| 0.0 | −0.05 | −0.04 | −0.04 | −0.04 | −0.04 |
| 2.00 | 5.1% | 3.7% | 4.0% | 3.7% | 4.3% |
| 3.89 | −1.5% | −1.0% | −1.1% | −1.0% | −1.2% |
| 12.54 | 0.1% | 0.0% | 0.0% | 0.0% | 0.0% |
| 26.57 | 0.0% | 0.0% | 0.0% | 0.0% | 0.0% |

TABLE 9D

CRP Residual Analyte Values
For Inverse Transformation in Reagent Optimization

| Analyte Value (mg/dL) | Particle/Antibody Concentration (mg/mL) | | | | |
|---|---|---|---|---|---|
| | 0.90 | 1.08 | 1.26 | 1.44 | 1.62 |
| 0.0 | 0.01 | 0.02 | 0.01 | 0.01 | 0.00 |
| 2.00 | −1.3% | −2.4% | −0.9% | −0.7% | 0.6% |
| 3.89 | 0.5% | 0.9% | 0.3% | 0.3% | −0.2% |
| 12.54 | −0.1% | −0.1% | 0.0% | 0.0% | 0.0% |
| 26.57 | 0.1% | 0.1% | 0.0% | 0.0% | 0.0% |

Figure 6:
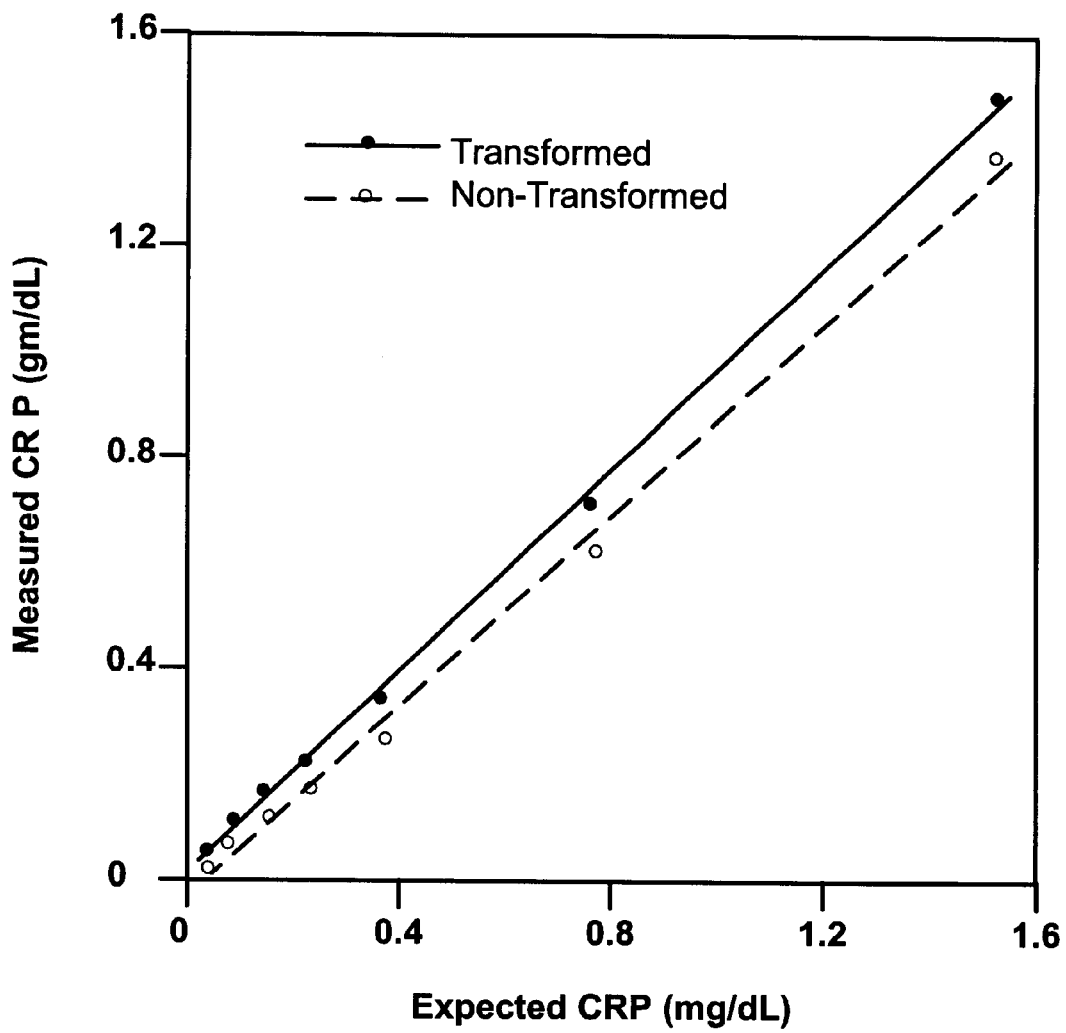
FIG. 6. shows correlation graphs and equations of the alternate embodiment of FIG. 4.

In order to challenge and test the low-end accuracy in this CRP example, serial dilution samples of a 1.6 mg/dL CRP solution were prepared. The theoretical values were plotted against the recovered values with and without the utilization of the double transformation. The correlation graphs and equations are shown in FIG. 6. Good recoveries were obtained at CRP concentrations between 0.00 and 1.6 mg/dL. The linear regression between the expected and measured concentrations in analyte units of mg/dL showed a better recovery of 0.94 when the double transformation process was used. As shown below and in FIG. 7, the linear regression between the expected and measured concentrations in analyte units of mg/dL showed a better recovery of 0.94 when the double transformation process was used.

Measured CRP with transformation=−0.015+0.94*Expected;

Measured CRP without transformation=−0.064+0.87*Expected;

EXAMPLE 6

CK-MB

A CK-MB assay is a solid phase enzyme immunoassay intended to quantitatively measure the MB isoenzyme of creatine kinase, CK, in human serum and plasma for confirmation of acute myocardial infarction. Such an assay is exemplary of an enzyme based immunoassay using the calibration method of the present invention. In the assay, patient sample is mixed with chromium dioxide particles coated with monoclonal antibodies specific for the CK-B subunit, and conjugate reagent (a beta-galactosidase labeled monoclonal antibodies specific for CK-MB isoenzyme). A particle/CKMB/conjugate sandwich forms during the incubation period. Unbound conjugate is washed and transferred into an assay test container containing chlorophenol red-beta-d-galactosidase (CPRG). The bound beta-galactosidase catalyzes the hydrolysis of CPRG to chlorophenol red (CPR). The color change measured at 577 nm using a standard spectrophotometer due to formation of CPR is directly proportional to the CK-MB concentration in the patient sample reported in units of ng/mL or ug/dL.

Standard curves showing the immunoassay signal generated by different calibrator solutions of CK-MB are shown in Table 10A for three types of data output, in a manner similar to those of the prealbumin assay of Example 1. Data in the Actual Signal Value column represent untreated or raw signals from the analyzer. The third column contains the results of modifying the actual signals using Equation 1 to produce an Inverse Transformation standard curve, using transform constants a=10,000 and b=10, of the present invention. The fourth column contains the results of modifying the actual signals using Equation 2 to produce a Complex Transformation standard curve, using transform constants a=−10,000, b=10, and c=1050 of the present invention.

TABLE 10A

CK-MB Standard Curves for Actual Signal,
Inverse Transformation and Complex Transformation

| Sample Value (ng/mL) | Actual Signal Value (mA) | Inverse Transformation (Equation 1) | Complex Transformation (Equation 2) |
|---|---|---|---|
| 0.0 | −0.1 | 1013.2 | 36.8 |
| 10.0 | 9.7 | 506.6 | 543.4 |
| 49.0 | 53.5 | 157.6 | 892.4 |
| 143.0 | 191.0 | 49.8 | 1000.2 |
| 335.0 | 524.8 | 18.7 | 1031.3 |

In order to evaluate the accuracy of using standard curves for the three types of data shown in Table 10A, analyte residual values were determined, as shown in Table 10B. Residual values for the actual signal standard curve are greater at lower levels of analyte concentration because this is an exemplary use of the present invention in an assay having a negative standard curve. However, when the analyzer signals are transformed by the Inverse or the Complex Transformation processes, marked improvements in accuracy are seen in the lower range of analyte concentrations. At the high-end of the standard curves, slightly higher residuals are observed; however, these are all within an acceptable limit of 5%.

TABLE 10B

CK-MB Residual Analyte Values for Actual Signal,
Inverse Transformation and Complex Transformation

| Sample Value (ng/mL) | Actual Signal Value | Inverse Transformation | Complex Transformation |
|---|---|---|---|
| 0.0 | 0.041 ng/mL | 0.000 ng/mL | 0.000 ng/mL |
| 10.0 | −0.4% | −0.1% | −0.1% |
| 49.0 | −0.0% | 0.6% | 0.6% |
| 143.0 | 0.0% | −3.5% | −3.5% |
| 335.0 | 0.0% | 4.5% | 4.5% |

EXAMPLE 7

FT4

Free thyroxine, FT4, is a thyroid function test that measures the fraction of T4 that is not protein bound but is physiologically available. Such an assay is exemplary of a heterogeneous immunoassay using the calibration method of the present invention wherein chromium dioxide particles with immobilized anti-T4 antibody are employed as a separation solid phase. A thyronine-alkaline phosphatase conjugate (T3-AlkP) is provided as FT4 conjugate reagent. During the assay, free T4 from a sample to be analyzed is incubated with a FT4 chromium dioxide particle based reagent and the FT4 conjugate reagent. A low level of free T4 present in the mixture allows a high level of the T3-AlkP to bind with the chromium dioxide particles, resulting in high enzyme level. Conversely, a high level of free T4 would allow a low level of the conjugate to bind with the chromium dioxide particles and resulting in low enzyme level. The level of enzyme may be detected via a cascade based signal generation process. The result is a negative calibration curve which is fit by non-linear regression using the logit model and then used to compute final test results in analyte units of ng/dL or pmol/L.

Standard curves showing the immunoassay signals generated using FT4 calibrator standards are shown in Table 11A for three types of data output, in a manner similar to those of the prealbumin assay of Example 1. Data in the Actual Signal Value column represent untreated or raw signals from a typical spectrophotometer analyzer. The third column contains the results of modifying the actual signals using Equation 1 to produce an Inverse Transformation standard curve, using transform constants a=100,000 and b=40, of the present invention. The fourth column contains the results of modifying the actual signals using Equation 2 to produce a Complex Transformation standard curve, using transform constants a=−10,000, b=40, and c=600 in accordance with the present invention.

TABLE 11A

FT4 Standard Curves for Actual Signal
Inverse Transformation and Complex Transformation

| Sample Value (ug/dL) | Actual Signal Value (mA) | Inverse Transformation (Equation 1) | Complex Transformation (Equation 2) |
|---|---|---|---|
| 0.03 | 681.0 | 138.7 | 461.3 |
| 0.77 | 507.0 | 182.8 | 417.2 |
| 1.59 | 369.0 | 244.5 | 355.5 |
| 3.13 | 255.0 | 339.0 | 261.0 |
| 6.65 | 130.0 | 588.2 | 11.8 |

Analyte residual values were determined and summarized in Table 11B. Residual values for the actual signal standard curve show greater deviation at lower levels of analyte concentration. When the analyzer signals are transformed by the Inverse or the Complex Transformation processes, one continues to observe marked improvement in accuracy as seen in the residual improvement from −1.2% to −0.1% at level 6.65 ug/mL. At the high-signal low-analyte portion of the standard curves, either equivalent or better residuals are also observed.

TABLE 11B

FT4 Residual Analyte Values for Actual Signal,
Inverse Transformation and Complex Transformation

| Sample Value (ug/dL) | Actual Signal Residual (ug/mL or % ug/dL) | Inverse Transformation (Equation 1) | Complex Transformation (Equation 2) |
|---|---|---|---|
| 0.03 | −10.4% | −2.6% | 10.8% |
| 0.77 | 3.6% | 5.9% | 5.8% |
| 1.59 | −4.7% | −5.2% | −5.4% |
| 3.13 | 3.1% | 1.4% | 1.4% |
| 6.65 | −1.2% | −0.1% | −0.1% |

It is to be understood that the embodiments of the invention disclosed herein are illustrative of the principles of the invention and that other modifications may be employed which are still within the scope of the invention. Accordingly, the present invention is not limited to those embodiments precisely shown and described in the specification but only by the following claims.

What is claimed is:

1. A method for calibrating an analyzer to perform an immunoassay for an analyte by:
   (a) measuring signal values using calibration solutions having known concentrations of the analyte to produce a first calibration curve;
   (b) transforming the measured signal values in the first calibration curve to produce a second calibration curve using an equation having the general form $x=a/(y+b)$, wherein:
   $x$=transformed signal values in the second calibration curve;
   $y$=measured signal values in the first calibration curve;
   $a$=a first constant which affects amplitude of the second calibration curve; and
   $b$=a second constant which affects curvature of the second calibration curve
   (c) using the second calibration curve to calibrate the analyzer.

2. A method for calibrating an analyzer to perform an immunoassay for an analyte by:
   (a) measuring signal values using calibration solutions having known concentrations of the analyte to produce a first calibration curve;
   (b) transforming the measured signal values in the first calibration curve to produce a second calibration curve using an equation having the general form $x=c+a/(y+b)$, wherein:
   $x$=transformed signal values in the second calibration curve;
   $y$=measured signal values in the first calibration curve;
   $a$=a first constant which affects amplitude of the second calibration curve;
   $b$=a second constant which affects curvature of the second calibration curve; and
   $c$=a third constant which controls location of transformed signal values in the second calibration curve
   (c) using the second calibration curve to calibrate the analyzer.

3. The method of claim 1 wherein the first calibration curve is a positive standard curve.

4. The method of claim 1 wherein the first calibration curve is a negative standard curve.

5. The method of claim 2 wherein the first calibration curve is a positive standard curve.

6. The method of claim 2 wherein the first calibration curve is a negative standard curve.

7. The method of claim 1 wherein the immunoassay is an agglutination immunoassay, an enzyme immunoassay, or a heterogeneous immunoassay.

8. The method of claim 2 wherein the immunoassay is an agglutination immunoassay, an enzyme immunoassay, or a heterogeneous immunoassay.

9. The method of claim 1 wherein the analyte is selected from the group consisting of prealbumin, Immunoglobulin A, Immunoglobulin G, Immunoglobulin M, valproic acid, C-reactive protein, the MB isoenzyme of creatine kinase, and free thyroxine.

10. The method of claim 2 wherein the analyte is selected from the group consisting of prealbumin, Immunoglobulin A, Immunoglobulin G, Immunoglobulin M, valproic acid, C-reactive protein, the MB isoenzyme of creatine kinase, and free thyroxine.

11. The method of claim 9 further including the addition of free antibodies specific to each analyte selected from said group so as to minimize analyte residual values.

12. The method of claim 11 wherein antibodies are added in two steps comprising a first addition of a smaller size portion of the total sample volume and a later addition of a remaining larger size portion of the total sample volume and measured signal values in the first calibration curve are obtained after each addition and compared with one another to indicate the presence of an antigen excess condition.

13. The method of claim 1 wherein the measured signal values in the first calibration curve are obtained from a combination of the low end portion of a first reaction rate curve and the higher end portion of an extrapolated reaction rate curve, the first reaction curve generated using a larger size portion of the total sample volume and the extrapolated reaction rate curve obtained from a combination of the first curve and a second reaction rate curve representative of the same sample of a smaller size portion of the total sample volume.

14. The method of claim 12 wherein the antigen is C-reactive protein.

* * * * *